United States Patent
Aflatoon (10) Patent No.: US 8,894,651 B2
(45) Date of Patent: Nov. 25, 2014

(54) METHOD OF LATERAL FACET APPROACH, DECOMPRESSION AND FUSION USING SCREWS AND STAPLES AS WELL AS ARTHROPLASTY

(76) Inventor: Kamran Aflatoon, Corona del Mar, CA (US)

(*) Notice: Subject to any disclaimer, the term of this patent is extended or adjusted under 35 U.S.C. 154(b) by 1381 days.

(21) Appl. No.: 12/283,438

(22) Filed: Sep. 11, 2008

(65) Prior Publication Data
US 2009/0099602 A1 Apr. 16, 2009

Related U.S. Application Data

(60) Provisional application No. 60/993,233, filed on Sep. 11, 2007.

(51) Int. Cl.
| | | |
|---|---|---|
| *A61B 17/84* | (2006.01) | |
| *A61B 17/86* | (2006.01) | |
| *A61B 17/16* | (2006.01) | |
| *A61B 17/70* | (2006.01) | |
| *A61F 2/30* | (2006.01) | |
| *A61F 2/44* | (2006.01) | |
| *A61B 19/00* | (2006.01) | |
| *A61B 17/02* | (2006.01) | |
| *A61B 17/34* | (2006.01) | |

(52) U.S. Cl.
CPC ..... *A61B 17/3468* (2013.01); *A61F 2002/3085* (2013.01); *A61F 2002/30576* (2013.01); *A61F 2/4455* (2013.01); *A61F 2/4405* (2013.01); *A61B 17/8625* (2013.01); *A61F 2002/30784* (2013.01); *A61B 2019/481* (2013.01); *A61B 2017/0256* (2013.01); *A61B 17/3421* (2013.01); *A61B 17/7064* (2013.01); *Y10S 606/914* (2013.01); *Y10S 606/915* (2013.01)
USPC ................ 606/75; 606/301; 606/80; 606/90; 606/914; 606/915

(58) Field of Classification Search
CPC .......... A61B 17/0642; A61B 17/7044; A61B 17/7064; A61B 17/8061; A61B 17/809
USPC ............ 606/301–321, 247, 297, 75, 914, 915
See application file for complete search history.

(56) References Cited

U.S. PATENT DOCUMENTS

| | | |
|---|---|---|
| 4,913,134 A | 4/1990 | Luque |
| 5,084,049 A | 1/1992 | Asher et al. |

(Continued)

OTHER PUBLICATIONS

EBI® VueLock® Anterior Cervical Plate System, Spine Universe, http://www.spineuniverse.com/displayarticle.php/article2992.html, (last visited Dec. 10, 2008).

(Continued)

*Primary Examiner* — Michael T Schaper
(74) *Attorney, Agent, or Firm* — Ober, Kaler, Grimes & Shriver; Royal W. Craig; Christopher F. Lonegro (57) ABSTRACT

A method of performing vertebral facet fusion by lateral approach and related devices. The lateral approach to facet fusion involves identifying the lateral mass and then introducing any of the fixation methods known or described herein laterally at one or more facets through the use of a hollow cannula. A surgical bone staple have a perforated bridge is used across the lateral facet joint where fixation is required. Where fusion is desired, a bone screw have lateral perforations of the shank is inserted through the bridge perforation at the joint to promote fusion. The staple and screw may be used in conjunction with one another or individually. The facet joint may be distracted prior to fixation to increase the foraminal space and decompress the neural structures to relieve pain. The method involves less surgical time, reduced blood loss and discomfort for the patient as compared to the posterior approach.

7 Claims, 11 Drawing Sheets

(56) References Cited

U.S. PATENT DOCUMENTS

| | | | |
|---|---|---|---|
| 5,129,899 A | 7/1992 | Small et al. | |
| 5,176,679 A | 1/1993 | Lin | |
| 5,261,910 A | 11/1993 | Warden et al. | |
| 5,334,204 A * | 8/1994 | Clewett et al. | 606/312 |
| 5,364,399 A | 11/1994 | Lowery et al. | |
| 5,380,324 A | 1/1995 | Muller et al. | |
| 5,527,312 A | 6/1996 | Ray | |
| 5,558,674 A | 9/1996 | Heggeness et al. | |
| 5,603,713 A | 2/1997 | Aust et al. | |
| 5,616,144 A | 4/1997 | Yapp et al. | |
| 5,676,666 A | 10/1997 | Oxland et al. | |
| 5,904,683 A | 5/1999 | Pohndorf et al. | |
| 6,068,632 A * | 5/2000 | Carchidi et al. | 606/79 |
| 6,106,526 A | 8/2000 | Harms et al. | |
| 6,120,503 A | 9/2000 | Michelson | |
| 6,224,602 B1 | 5/2001 | Hayes | |
| 6,231,610 B1 | 5/2001 | Geisler | |
| 6,342,055 B1 | 1/2002 | Eisermann et al. | |
| 6,364,880 B1 * | 4/2002 | Michelson | 606/247 |
| 6,436,142 B1 | 8/2002 | Paes et al. | |
| 6,454,771 B1 | 9/2002 | Michelson | |
| 6,482,232 B1 * | 11/2002 | Boucher et al. | 623/13.14 |
| 6,695,845 B2 | 2/2004 | Dixon et al. | |
| 6,830,571 B2 | 12/2004 | Lenke et al. | |
| 2002/0045899 A1 | 4/2002 | Errico et al. | |
| 2002/0173790 A1 | 11/2002 | Chang et al. | |
| 2002/0183756 A1 | 12/2002 | Michelson | |
| 2003/0036759 A1 | 2/2003 | Musso | |
| 2003/0208204 A1 | 11/2003 | Bailey et al. | |
| 2005/0021032 A1 | 1/2005 | Koo | |
| 2005/0055026 A1 * | 3/2005 | Biedermann et al. | 606/73 |
| 2005/0059971 A1 | 3/2005 | Michelson | |
| 2005/0137597 A1 | 6/2005 | Butler et al. | |
| 2005/0177161 A1 | 8/2005 | Baynham et al. | |
| 2005/0192576 A1 | 9/2005 | Michelson | |
| 2006/0241597 A1 | 10/2006 | Mitchell et al. | |

OTHER PUBLICATIONS

New Anterior Cervical Plate Makes Headlines, http://www.spineuniverse.com/displayarticle.php/article1535.html, (last visited Dec. 10, 2008).

Reflex Anterior Cervical Plate System, Stryker Corporation, http://www.stryker.com/en-us/products/Spine/Cervical/index.htm (last visited Dec. 10, 2008).

* cited by examiner

METHOD OF LATERAL FACET APPROACH, DECOMPRESSION AND FUSION USING SCREWS AND STAPLES AS WELL AS ARTHROPLASTY

CROSS-REFERENCE TO RELATED APPLICATIONS

The present application derives priority from provisional application 60/993,233 filed on Sep. 11, 2007 which is incorporated herein by reference.

BACKGROUND OF THE INVENTION

1. Field of the Invention

The present invention relates to a method of approach to the lateral cervical facet for the purposes of spondylosyndesis or arthoplasty techniques as well as related devices.

2. Description of the Background

Human spinal degeneration is a natural result of aging and may lead to a medical condition known as spinal stenosis in which the spinal canal narrows and compresses the spinal cord and neural structures. Spinal stenosis is often accompanied or even caused by a herniated intervertebral disk. Patients suffering from the condition often experience significant pain and limited range of motion and mobility. Laminectomy is a surgical procedure for treating spinal stenosis in which one or both lamina are removed, often along with the spinal process, in order to relieve the pressure on the spinal cord and the related pain. Unfortunately, this procedure suffers from one major drawback, namely that it can compromise the stability of the spine, particularly when performed in the cervical region of the spine but also in the lumbar and thoracic regions as well.

Cervical facet fusion is a procedure in which the facet joints between two or more vertebra are joined together to stabilize the spine and eliminate motion which may contribute to spondylosis, or continued degeneration, and prevent progressive deformity. Cervical facet fusion is commonly performed in conjunction with laminectomy. Toward this end, recent technological advances have facilitated disc replacement and have paved the way for potential facet replacement. One of the major contraindications for disc arthroplasty is degeneration of the facet. By replacing the facet or resurfacing it, patients can benefit from this emerging technology.

The standard approach for decompressive laminectomy, facet fusion and/or facet replacements is the posterior approach, and may be performed through variety of methods. The classic method involves passing wires through drill holes in the articular processes and binding two longitudinal struts of bone to the posterior columns of the articular processes. Another technique uses lateral mass screws that are connected via a metal rod. However, regardless of the method used, the posterior approach for posterolateral cervical facet fusion is time-consuming, results in resection of important connective tissue and musculature, involves moderate blood loss and often results in the patient suffering from shoulder pain for a significant period after surgery. Posterior approach patients also usually require inpatient hospital care for 2 to 3 days, require drains and experience high incidence of surgical site infection.

A variety of devices from different manufacturers have been developed for utilization in spinal surgeries such as facet fusion. Many of these devices are intended for fusion or fixation of the vertebra in the cervical region and elsewhere. These devices commonly consists of one or more plates and screws, pegs, or rods with fixating connectors that may be joined to the bone in order to stabilize the spine. Other devices take the form of a staple. Considerable effort has been expended on preventing the counter-rotation and withdrawal of screws as well as the ability of the devices to secure adjacent vertebra. Considerably less effort has been expended on making such devices less intrusive and quicker to implant (while still maintaining efficacy).

Although the noted spinal fixation devices as well as others have furthered technological development, none are done through lateral cervical approach and none provide a small profile of fixation, decompression or arthroplasty. It would thus be advantageous to provide a cervical staple, screw fusion fixation or arthroplasty for lateral cervical facet joint that: (1) allows for a more precise and a much smaller profile of fixation than prior art devices, (2) imposes less blood loss, (3) minimizes surgical time (4) avoids traction on the esophagus and trachea as in the anterior approach, (5) is minimally invasive, (6) is lightweight, and (7) is inexpensive to manufacture and sell to provide for widespread use.

A novel lateral approach is herein proposed for facet decompression, fusion or arthroplasty that avoids many of the drawbacks of the known approaches. The lateral approach is done through a minimally invasive method, offers direct access to the facet joint, provides secure stabilization, and permits early mobilization of the patient.

The present applicant has submitted a copending patent application for facet replacement using the lateral approach for the purpose of inserting a resurfacing material.

SUMMARY OF THE INVENTION

Accordingly, it is an object of the invention to provide a surgical screw including holes or perforations along the threaded body and central shaft of the screw to allow bone growth there through and facilitate fusion of a facet joint.

Another object is to provide a quick solid fixation staple and method to add stability to the spine in patients who have not had prior surgical stabilization of the spine or for patients who have previously undergone surgical fusion anteriorly. Another object is to provide a decompressive resurfacing possibility for facet degeneration.

An additional object is to provide a cervical staple and a surgical screw that are inexpensive to manufacture and sell to provide for widespread use.

Yet another object is to provide a method of lateral cervical facet fusion, which is a minimally invasive surgical method and that reduces attending staff requirements and operative time.

These and other objects are accomplished by a lateral approach to facet fusion which involves less surgical time, reduced blood loss and discomfort for the patient as compared to the posterior approach. The lateral approach to facet fusion involves identifying the lateral mass and then introducing any of the fixation methods known or described herein laterally at one or more facets through the use of a hollow cannula. A surgical bone staple is used across the lateral facet joint where fixation is required. Where fusion is desired, a bone screw have lateral perforations of the shank is inserted at the joint to promote fusion. The staple and screw may be used in conjunction with one another or individually. The facet joint may be distracted prior to fixation to increase the foraminal space and decompress the neural structures to relieve pain.

BRIEF DESCRIPTION OF THE DRAWINGS

Other objects, features, and advantages of the present invention will become more apparent from the following detailed description of the preferred embodiment and certain modifications thereof, in which.

DETAILED DESCRIPTION OF THE PREFERRED EMBODIMENTS

The present invention provides for a minimally invasive surgical implantation method and apparatus for cervical spine implants that preserves the structure and to a limited degree the function of the spine. In addition to stabilization, embodiments of the invention provide for distracting the cervical vertebra to increase the foraminal space and relieve pain by reducing pressure on the neural structures and blood vessels of the cervical spine.

Two facet joints are formed between each vertebrae of the spine. Each vertebra has two superior articulating facets and two inferior articulating facets, with the superior facet of a lower vertebra and an inferior facet of an upper vertebra meeting and aligning to form one facet joint on each side of the spine. In the cervical spine, the upward inclination of the superior articular surfaces of the facet joints allows for considerable flexion and extension, as well as for lateral mobility. Each facet joint is covered by a dense, elastic articular capsule that is lined by a synovial membrane that secretes synovial fluid to lubricate the facet joint. The exterior of the joint capsule is surrounded by a capsular ligament that must be cut or displaced as part of some embodiments of the presently disclosed method for fusing the facet joints. In a preferred embodiment of the present invention, the implanted fusion screw can cause interfacet distraction that increases foraminal dimension if desired.

Figure 1:
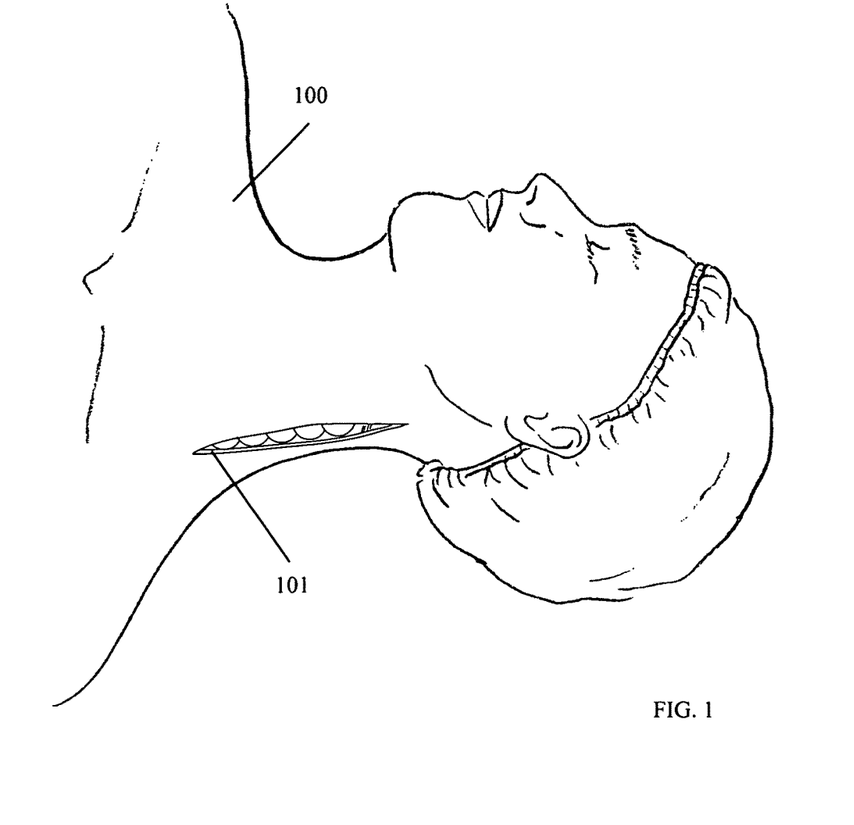
FIG. 1 is a perspective view of a patient indicating the dermal incision for lateral approach.
Figure 2:
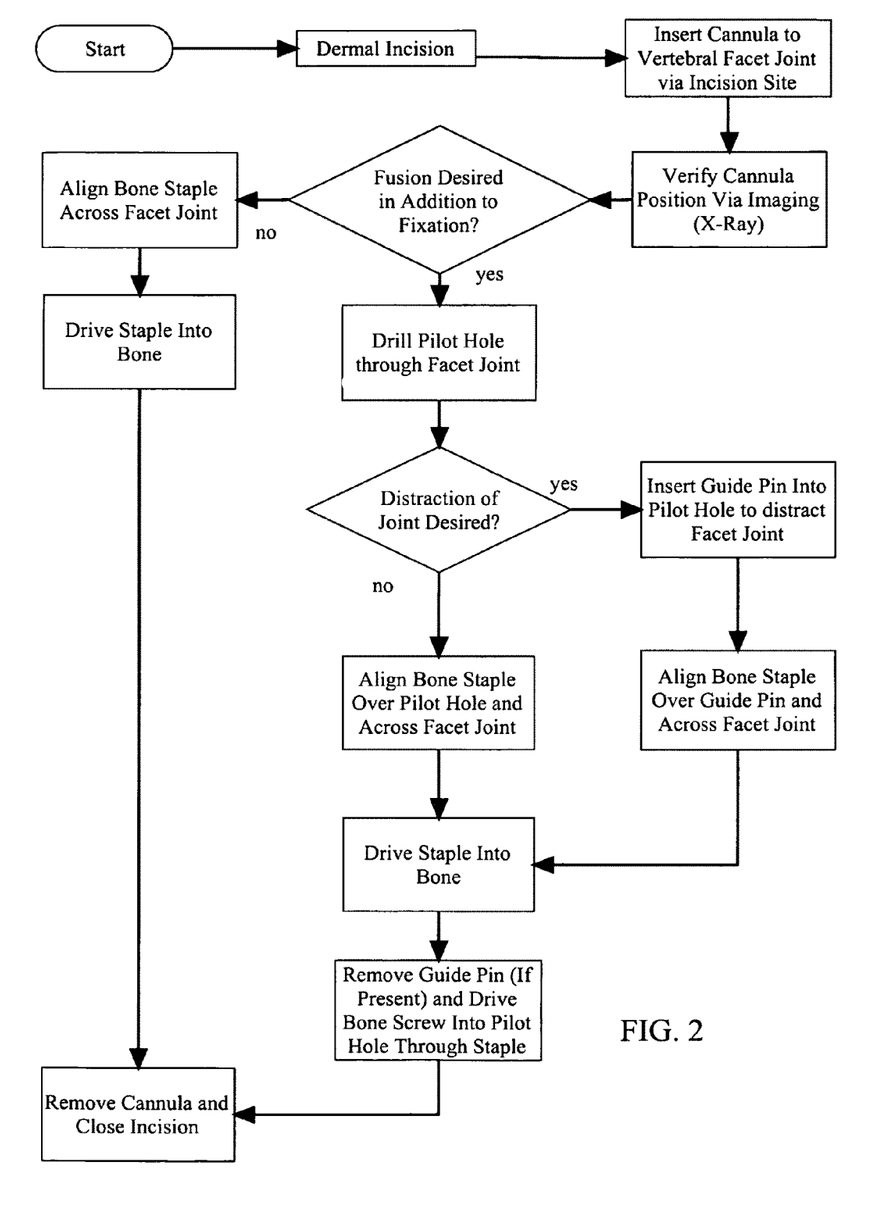
FIG. 2 is a diagram of the steps for lateral facet approach, decompression, and fusion using screws and staples

FIG. 1 depicts the neck region of a patient 100 indicating the position of the dermal incision 101 for lateral approach. With reference to FIG. 2, after initial incision a cannula is inserted past the medial or posterior scalenes or trapezius muscle, depending on the particular cervical vertebra to be fused, to reach the intended facet joint or joints. The cannula is used to allow easy docking without any impingement on the surrounding structures. The spinal accessary nerve is the only critical structure in the area that should be avoided. Injury to the nerve will cause paralysis of the scapula muscles. The cannula that is inserted should be smooth with blunt tip in order to avoid damage to the nerve. The location of the cannula in relation to the facet joint is monitored and verified by medical imaging techniques such as X-ray imaging. Most desirably surgical direct semiconductor detection is used to provide real time monitoring.

Figure 4:
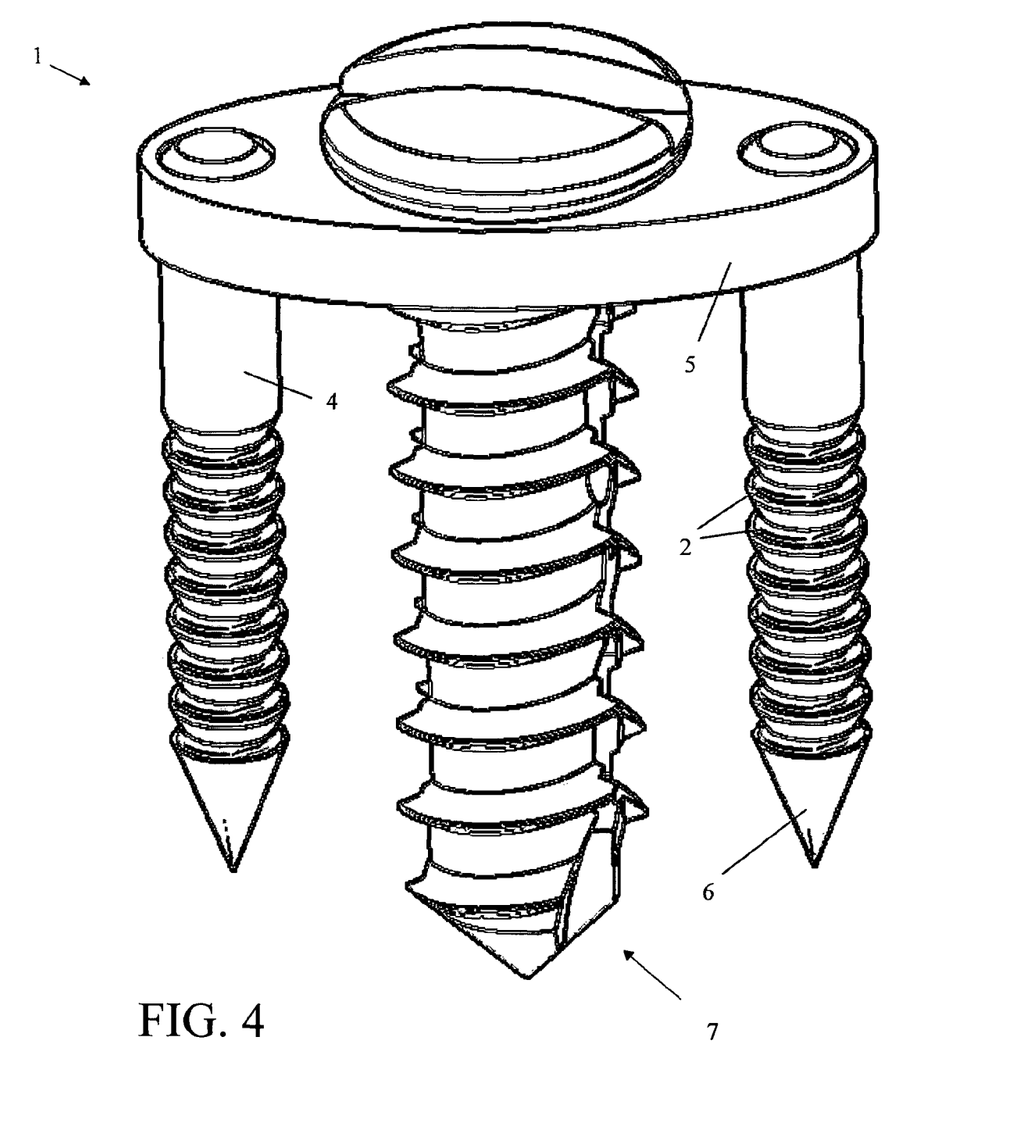
FIG. 4 is a side above perspective view of the screw in conjunction with the staple.
Figure 5:
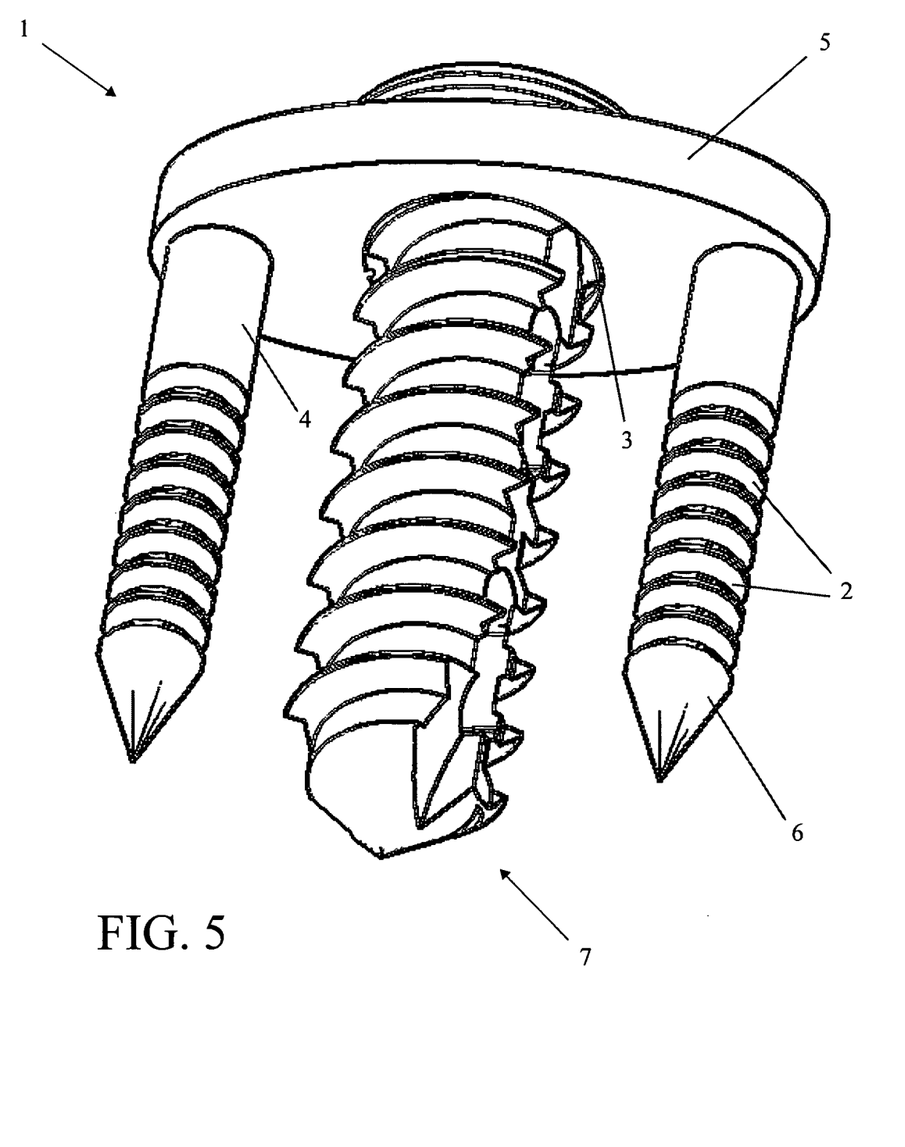
FIG. 5 is a side below perspective view of the screw in conjunction with the staple.

Once the cannula is in position and where fixation is desired without distraction or fusion, a staple 1, as depicted in FIGS. 4 and 5 and further described below, is inserted over the facet joint via the cannula with the distal points 6 penetrating the bone by force. Force may be applied by surgical bone hammer or other known surgical techniques. Where fixation and fusion are desired a surgical bone drill and bit may be inserted to drill a pilot hole into the facet joint. The drill has a sleeve on the shaft to limit penetration into the joint and thus the depth of the hole, based on the particular physiology of the vertebra. Ideally the hole is oriented within and across the primary plane of the joint. A staple 1, again as depicted in FIGS. 4 and 5 and further described below, is inserted over the facet joint via the cannula with the distal points 6 penetrating the bone by force. Force may be applied by surgical bone hammer or other known surgical techniques. Staple 1 should be position such that hole 3 in the staple bridge 5 aligns with the pilot hole drilled in the facet joint.

Figure 3:
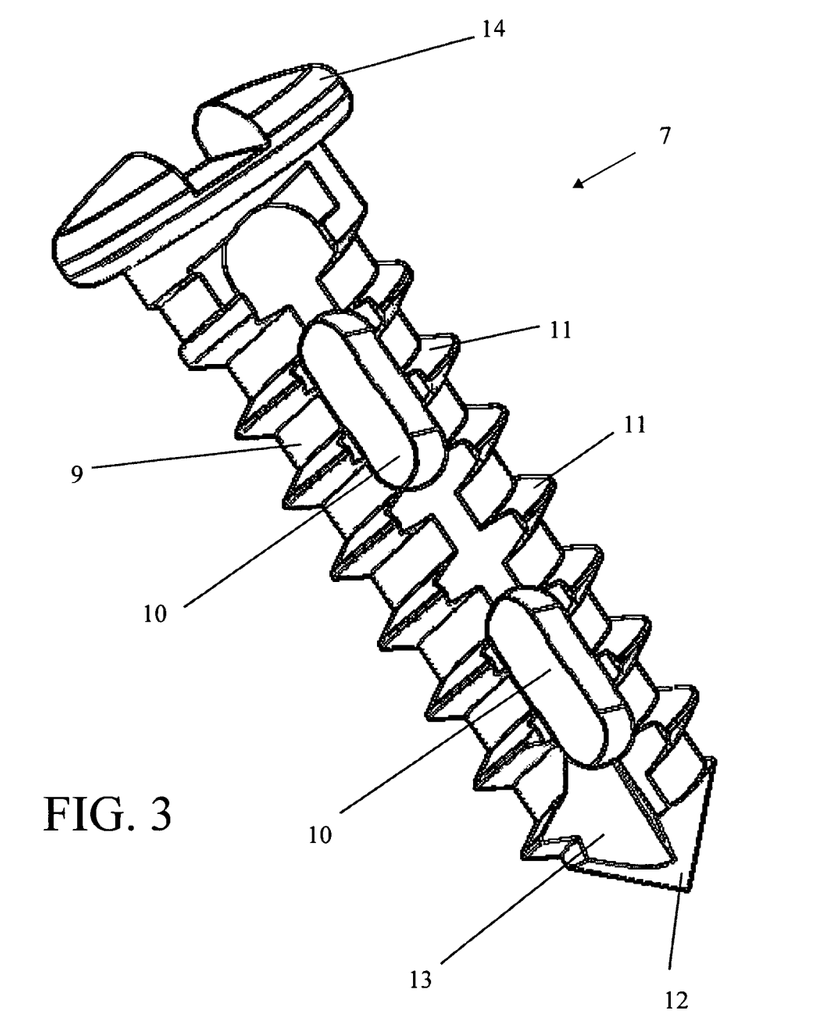
FIG. 3 is a front perspective view of the screw.

A bone screw 7, as depicted in FIGS. 3, 4 and 5 and further described below, is driven through hole 3 of the staple and into the pilot hole by a cooperative driving tool engaging screw head 14. The incision is then closed. Bone growth subsequent to implantation through and around the screw shank 9 and lateral perforations 10 serves to fuse the joint. Staple 1 will generally remain in position once fusion has been achieved.

Where distraction of the joint is desired prior to fixation, an alternate embodiment of the described method is employed. The previously described method is followed through the step of drilling a pilot hole in the facet joint. After drilling a pilot hole a guide pin is inserted into the hole to distract the joint. The guide pin has the same diameter as the screw 7 that will ultimately occupy the space but lacks the head 14 of the screw. The guide pin has a long shaft resembling a drill bit and is long enough to extend past the skin of the patient. The guide pin remains in place as a spacer to maintain distraction while staple 1 is inserted over the pin with the distal points 6 penetrating the bone by force as above. Once the facet joint is fixated by the staple the guide pin is removed and the bone screw is driven into the pilot hole as above. The incision is then closed.

In both embodiments the pilot hole bit diameter (and ultimately the resulting hole diameter) may be selected in cooperation with vertebral physiology to achieve a desired result. Where fusion of the facet is desired without distraction the docking hole diameter is selected to be equal to or only slightly smaller than the maximum diameter of the screw thread (described below). Where distraction is desired the docking hole and screw diameter may be selected cooperatively such that insertion of the guide pine into the hole will cause the facet joint to open or distract relieving pressure on the neural structures. In such a circumstance the docking hole should be undersized as compared to the screw. A tapered guide pin or screw may also be utilized to achieve this result. The bone screw of the present invention, as described below, is formed to promote bone growth around and through the screw and lateral facet joint, fusing the vertebra and stabilizing the spine.

In an alternate embodiment of the presented methods the pre-drilling of a pilot hole is eliminated and a self drilling screw is used to drill the bone of the facet joints during insertion. The screw may also be self reaming and/or self tapping to provide the desired hole diameter and facilitate distraction of the joint as described above. The diameter of the self drilling region or the self reaming region of the screw may be selected in relation to the shank and thread diameter to determine the amount of distraction and decompression.

Figure 7:
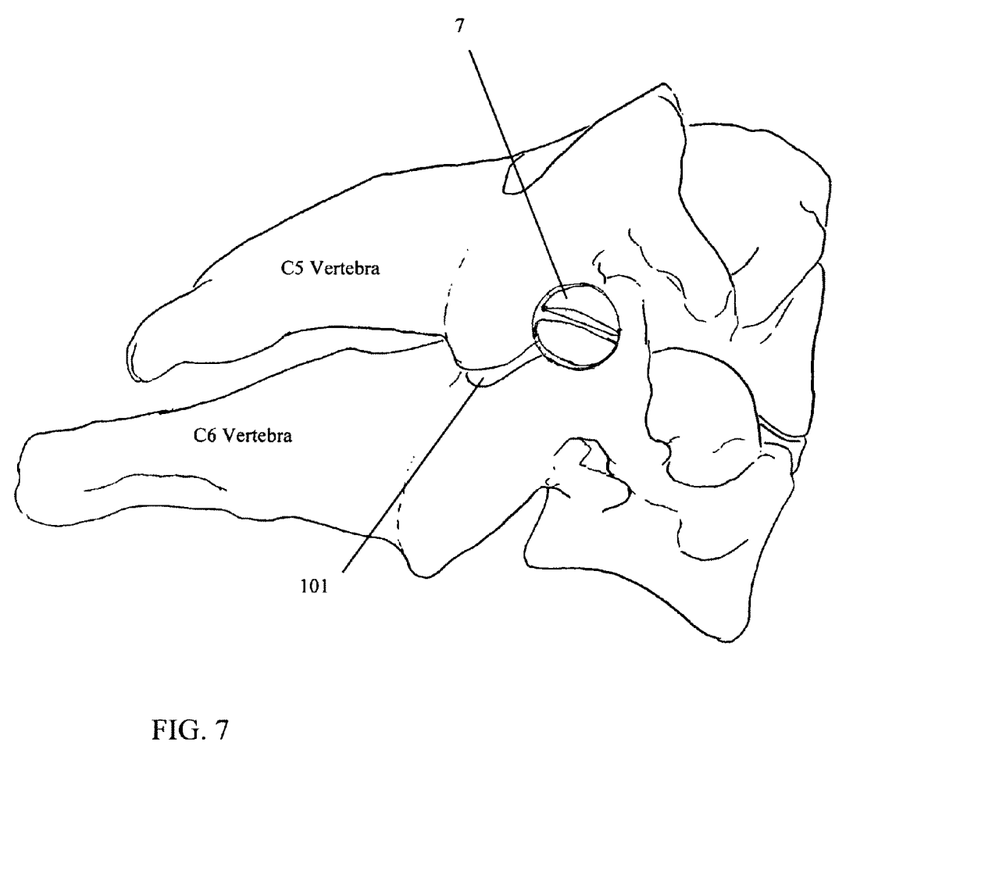
FIG. 7 is a side perspective view of the screw installed in the C5-C6 facet joint.
Figure 8:
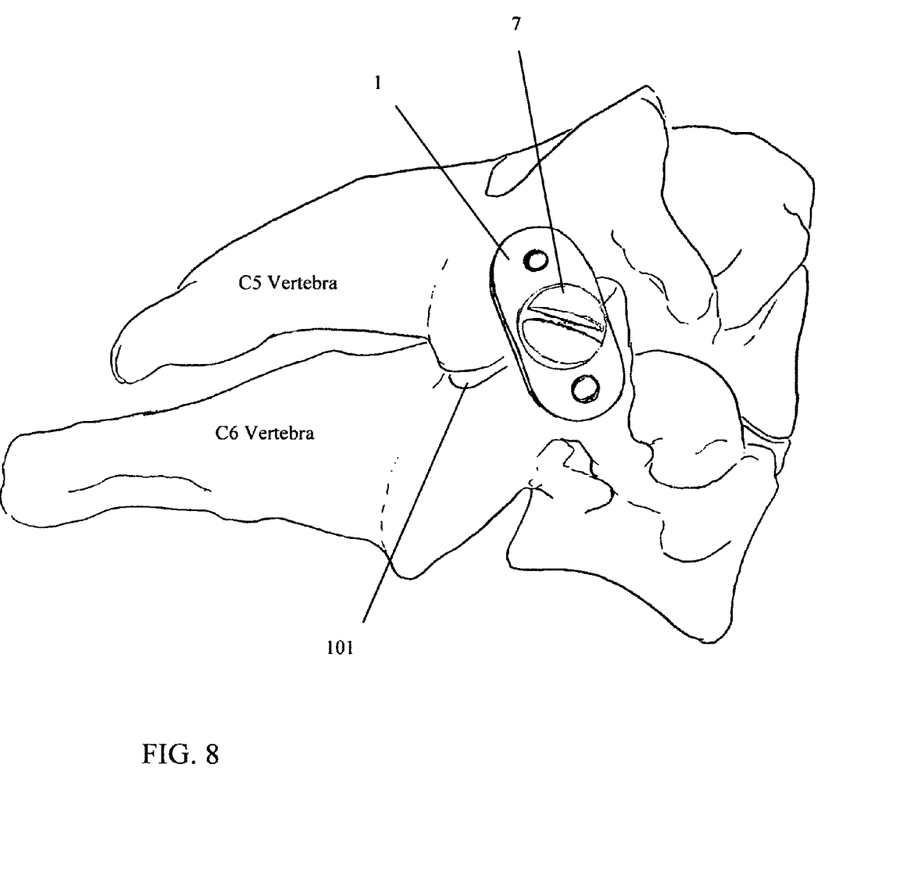
FIG. 8 is a side perspective view of the screw and staple installed at the C5-C6 facet joint
Figure 9:
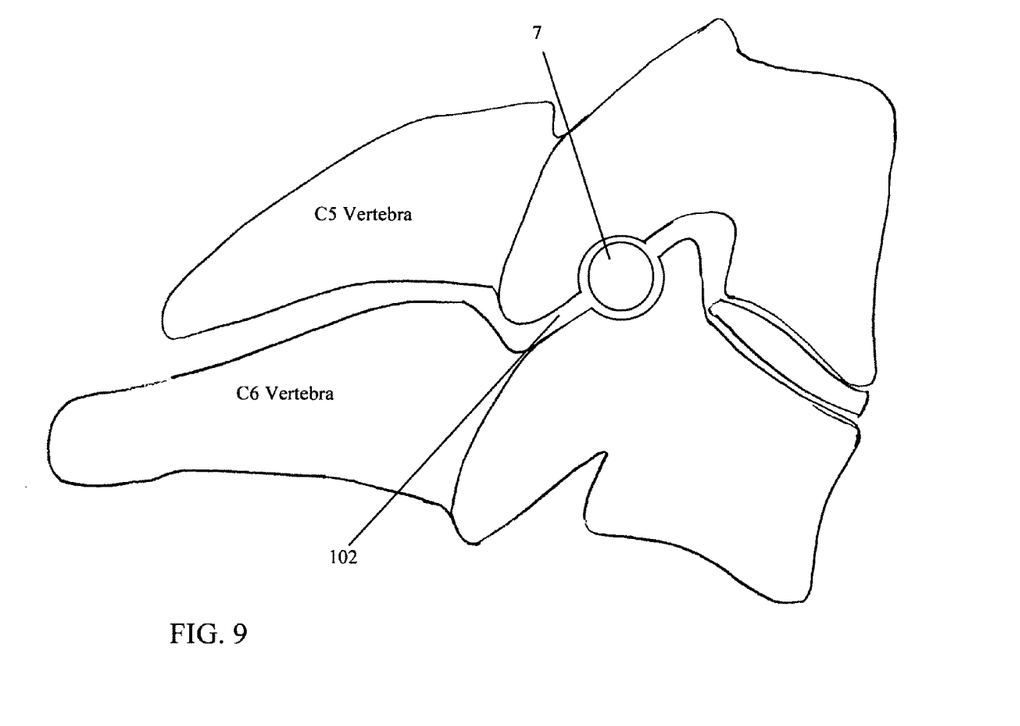
FIG. 9 is an abstracted section of the C5 and C6 vertebra showing the location of the screw.
Figure 10:
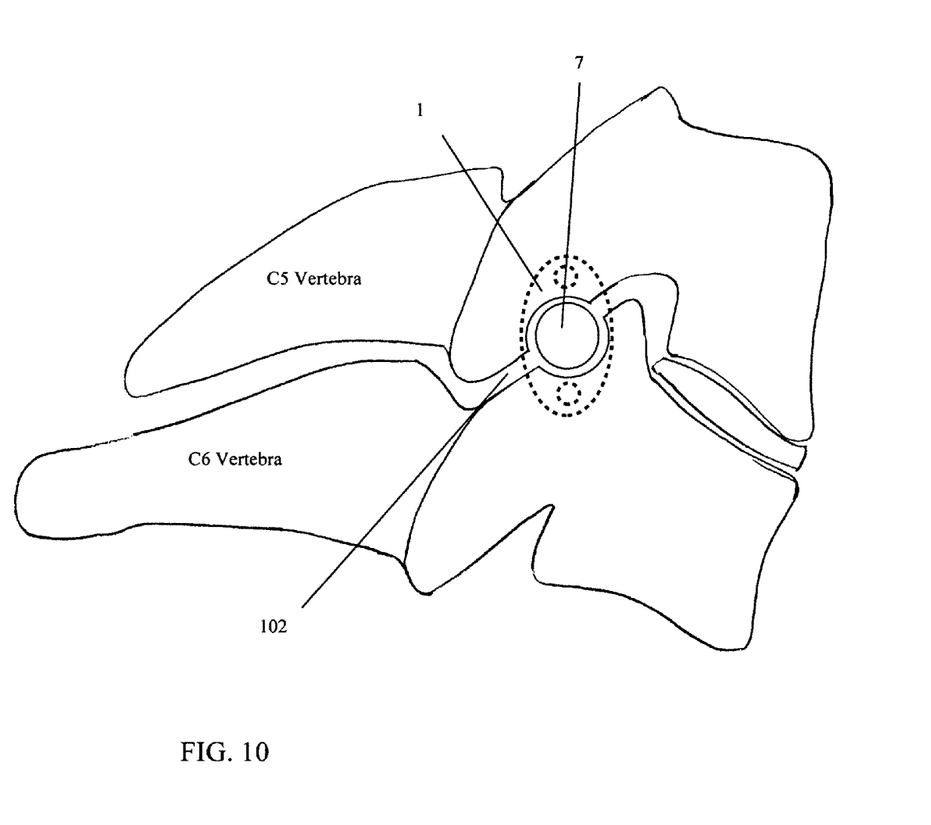
FIG. 10 is an abstracted section of the C5 and C6 vertebra showing the location of the screw and staple.

FIG. 8 depicts the location of bone screw 7 and staple 1 after implantation to stabilize the right C5-C6 facet joint 101. FIG. 10 is an abstraction of the C5-C6 vertebra indicating the position of the screw 7 and staple 1 in the facet joint 102. In an alternate embodiment of the present invention, depicted in FIGS. 7 and 9, the bone screw 7 may be utilized without the staple to promote fusion of the joint. As with the other embodiments of the present invention, this embodiment may be utilized at locations other than the cervical spine for bone or joint fusion. Similarly, in yet another embodiment, the staple 1 may be utilized without the screw 7 to quickly and minimally invasively fixate and stabilize a bone or joint in the cervical spine or elsewhere. This may be done to reinforce and/or re-stabilize the spine in a patient who has already had anterior fixation. It should be noted that the C5-C6 facet joint here is referenced by way of illustration and the present method may be utilized at other cervical and non cervical joints.

FIG. 3 is a perspective view of a bone screw 7 according to the present invention for use with the method of the present invention. The bone screw 7 is a screw having a cylindrical shank 9 topped at one end by a head 14. The head is adapted to be engaged by a fastener-driving tool such as a conventional screwdriver, hex driver, socket or other known driving method. The diameter of the head is larger than the shank. Shank 9 is encircled by along some or all of its length by external threads 11. Shank 9 of screw 7 may be hollow along some or all of its length. One or more perforations 10 through the shank 7 along its linear axis are provided to allow bone growth through the screw in order to fuse the joint into which it is driven. The distal tip of the screw may be blunt or may be tapered to a sharp point 12. In an alternate embodiment the screw the distal tip is provided with a blade 13 so as to be self drilling according to any known design. In yet another alternate embodiment a portion of the shank is provided with one or more blades so as to be self reaming.

Figure 6:
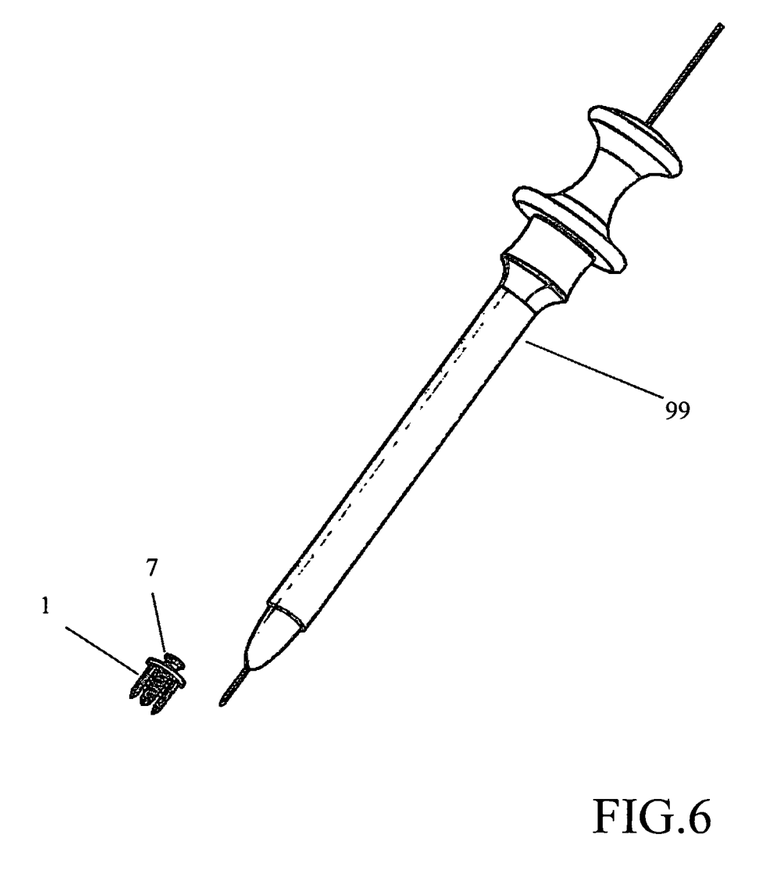
FIG. 6 is a side perspective view of the screw/staple combination relative to the cannula.

FIG. 4 and FIG. 5 are upper and lower perspective view of the screw 7 of the present invention in conjunction with a staple 1 of the present invention. FIG. 6 is perspective view of the cannula 99 utilized in the method of the present invention with screw 7 and staple 1. The staple 1 includes first and a second legs 4 each terminating in a beveled or pointed distal end 6 that is able to penetrate the bone, and interconnected at a proximal end by a bridge 6. Legs 4 and bridge six may be integrally formed or may be connected via known manufacturing techniques including welding, compression and mechanical integration. Preferably, as seen in FIG. 4, both legs are defined by a plurality of annual or outwardly oriented notches 2 formed with beveled walls defining a serrated outer surface. To perform the method disclosed herein the staple 1 may alternately resemble any known surgical staple, the embodiment of FIGS. 5 and 6 merely being exemplary. The staple may be utilized in the novel method of lateral facet fusion described above, and may be implanted in a matter of seconds with a small incision and driving the staple 1 by itself across the joint to eliminate motion. The staple's bridge 6 may have a hole 3 in the middle to allow the screw 7 or a similar screw to penetrate through the staple 1 and into the facet joint. Where fixation is intended without fusion as described above the staple bridge 6 would be solid without any hole 3.

Figure 11:
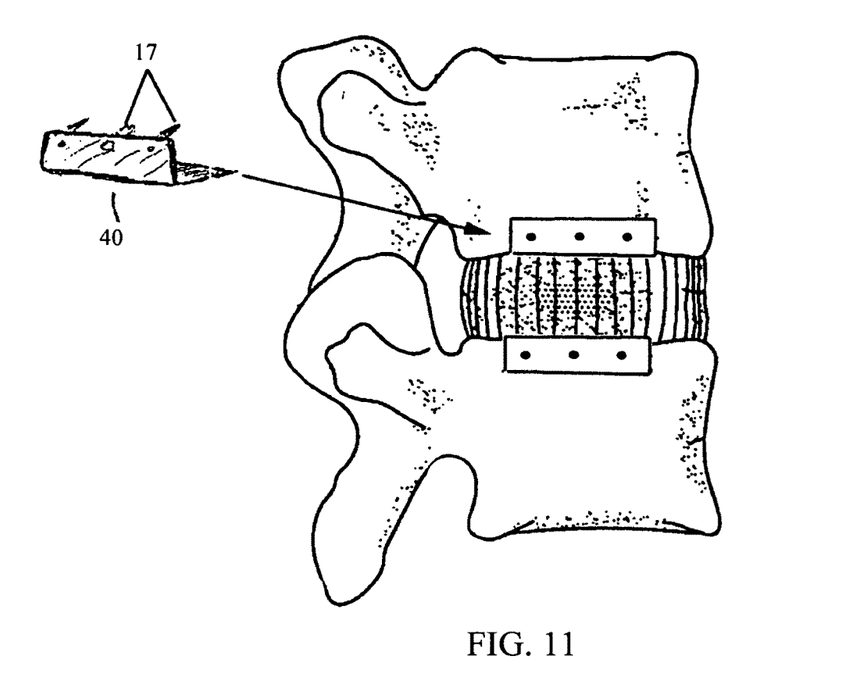
FIG. 11 is a side perspective view of a facet replacement plate 4.
Figure 12:
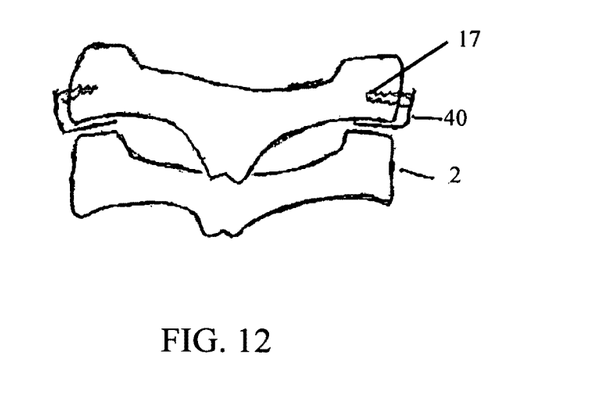
FIG. 12 is a front cross-section of the facet replacement plate 4.

A facet replacement plate 40 is also disclosed herein for use in the presently described method or independently. FIG. 11 is a side perspective view of a facet replacement plate 40 in the lumbar region. The FIG. 11 inset depicts the replacement plate 40 pre-implantation. FIG. 12 is a front cross-section of the facet replacement plate 40 in the cervical vertebra 2. The facet replacement plate 40 comprises a thin right-angle plate that is interposed in between the facet joint laterally and fixated to the bone above or below via a series of small screws 17 or nails. Screws 17 may be of the design described herein or of a conventional design. The right-angle plate 40 fits inside the facet joint and is fixated from outside by screws 17 or nails penetrating the bone.

All of the above components can be constructed of durable, surgically, implantable material such as titanium, stainless steel or PEEK.

The above-described lateral approach to facet fusion and related devices can be equally applied to other areas of the spine including the lumber and thoracic regions. Although the staple 1 and screw 7 have particular utility for the lateral approach to facet fusion, one skilled in the art will understand that the present invention can be equally applicable to other approaches to facet fusion and to fusion or fixation of other skeletal structures.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. A kit for decompression and fixation of a vertebral facet joint by dermal incision from a lateral approach, comprising:
   a drill bit for preparing a hole in said facet joint, the drill bit having a first diameter;
   a tapered pin having a second diameter greater than said first diameter for decompression of said facet joint by insertion into said hole, said pin having a length sufficient to extend outside of said dermal incision when inserted in said facet joint;
   a surgical staple comprising:
      a first leg and a second leg, each having a length and a first and second end;
      a bridge joining the first end of the first leg with the first end of the second kg, said bridge having an aperture situated between said legs for insertion over said pin and, after removal of said pin, for insertion of a bone screw;
      a sharp point situated at the second end of each leg; and
      a plurality of serrations along at least a portion of the length of said legs; and
   a hone screw comprising:
      a cylindrical shank having a first end and a second end, said shank having a diameter equal to said second diameter,
      a head affixed to said first end of said cylindrical shank and adapted to be engaged by a fastener-driving tool,
      the shank further comprising an externally-threaded portion for engagement with said facet joint, and
      at least one lateral perforation through said shank whereby bone growth may engage and secure the screw within the facet joint.

2. The kit of claim 1 wherein a tip extends from said second end of said shank, wherein the tip is in the form of a point.

3. The kit of claim 1 wherein said shank is hollow, said at least one lateral perforation allowing bone growth into and through said shank.

4. The kit of claim 1 wherein said sharp point is a beveled point.

5. The kit of claim 1 wherein said serrations are annular with respect to each leg.

6. The kit of claim 1 wherein said serrations are outwardly oriented.

7. The kit of claim 1 wherein said bridge is a plate.

* * * * *